United States Patent
Bowman et al.

(10) Patent No.: US 11,974,756 B2
(45) Date of Patent: *May 7, 2024

(54) EMBOLIC COIL AND DETACHMENT SYSTEM

(71) Applicant: MicroVention, Inc., Aliso Viejo, CA (US)

(72) Inventors: Heath Bowman, Aliso Viejo, CA (US); Nga-Ting Wong, Aliso Viejo, CA (US); Joseph Rye, Aliso Viejo, CA (US); Timothy Dalton, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,914

(22) Filed: Jul. 20, 2022

(65) Prior Publication Data
US 2022/0361888 A1 Nov. 17, 2022

Related U.S. Application Data

(63) Continuation of application No. 16/686,061, filed on Nov. 15, 2019, now Pat. No. 11,439,401.

(60) Provisional application No. 62/768,800, filed on Nov. 16, 2018.

(51) Int. Cl.
*A61B 17/12* (2006.01)
*A61B 17/00* (2006.01)

(52) U.S. Cl.
CPC .... *A61B 17/1215* (2013.01); *A61B 17/12113* (2013.01); *A61B 2017/00867* (2013.01); *A61B 2017/0088* (2013.01); *A61B 2017/0092* (2013.01); *A61B 2017/12063* (2013.01); *A61B 2017/1209* (2013.01)

(58) Field of Classification Search
CPC .......... A61B 17/1215; A61B 17/12113; A61B 2017/12063
See application file for complete search history.

(56) References Cited

U.S. PATENT DOCUMENTS

| | | |
|---|---|---|
| 10,806,462 B2 | 10/2020 | Lorenzo |
| 2004/0186464 A1 | 9/2004 | Mamayek et al. |
| 2005/0209633 A1 | 9/2005 | Callister et al. |
| 2007/0299422 A1 | 12/2007 | Inganas et al. |
| 2009/0163780 A1 | 6/2009 | Tieu |
| 2010/0331948 A1 | 12/2010 | Turovskiy et al. |
| 2013/0296917 A1 | 11/2013 | Rees |
| 2014/0094844 A1* | 4/2014 | Gulachenski ...... A61B 17/1214 29/428 |

(Continued)

*Primary Examiner* — Sarah A Long
*Assistant Examiner* — Raihan R Khandker
(74) *Attorney, Agent, or Firm* — Inskeep IP Group, Inc.

(57) ABSTRACT

Embolic coils with detachable segments that are separated by detachment capsules that are thermolytically degradable such that varying lengths of coil may be implanted into a vascular malformation to occlude same. The capsules are radiotransparent when compared to the adjoining coil segments to the location of the segments is easily seen. The capsules further include protruding electrical contacts that make positive contact with terminals on a delivery catheter. The terminals on the delivery catheter serve as markers so the relationship between the detachment capsules and the terminals is easily visible under x-ray.

17 Claims, 10 Drawing Sheets

(56) References Cited

U.S. PATENT DOCUMENTS

| | | | |
|---|---|---|---|
| 2015/0173772 A1* | 6/2015 | Bowman | A61B 17/1214 606/200 |
| 2019/0192162 A1 | 6/2019 | Lorenzo | |

* cited by examiner

EMBOLIC COIL AND DETACHMENT SYSTEM

RELATED APPLICATIONS

This application is a continuation and claims benefit of and priority to patent application Ser. No. 16/686,061, filed Nov. 15, 2019, entitled Embolic Coil And Detachment System, which claims benefit of and priority to U.S. Provisional Application Ser. No. 62/768,800 filed Nov. 16, 2018 entitled Embolic Coil, both of which are hereby incorporated herein by reference in their entireties.

BACKGROUND OF THE INVENTION

Embolic or occlusive coils are commonly used to occlude a target structure within a patient to prevent blood flow to the region. These coils are used to treat a variety of conditions, such as aneurysms. Treating aneurysms with coils involves filling the aneurysm with a length of coil, which becomes wadded up within the aneurysm, thus limiting open space within the aneurysm into which blood can flow. By limiting blood flow, the walls of the aneurysm are not subjected to potentially dangerous blood pressures. Additionally, blood clots are less likely to form and later escape through the neck of the aneurysm.

An aneurysm typically has a neck and a cavity, much like a balloon, and the embolic coil delivery procedure is complicated due to the variance in aneurysm sizes and shapes. It is important to completely fill the cavity with one or more coils and often several coils are required. If the cavity is not completely filled, the efficacy of the treatment is diminished, and the aneurysm will still be subjected to high blood pressures and may rupture. If too many coils are used, the coils will not remain contained within the aneurysm and may either migrate out of the aneurysm into the blood stream or begin to protrude from the neck of the aneurysm and impede blood flow through the adjoining vessel.

Coils that can be customized during implantation such that an ideal length can be created for any given aneurysm have been developed. These solutions are shown and described in U.S. Pat. No. 9,877,729 entitled CATHETER SYSTEM, issued on Jan. 30, 2018 to Bowman et al., and in U.S. Pat. No. 9,808,599, entitled DEVICE DELIVERY SYSTEM, issued Nov. 7, 2017 to Bowman et al., all of which are hereby incorporated by reference in their entireties.

During delivery of these coils, alignment between the electrical terminals of the delivery catheters, and the corresponding electrical contacts associated with the coils, is necessary to cause separation of the coil segments. Due to the small size of the coils, this alignment spans a short longitudinal distance. It would be beneficial to modify the electrical contacts associated with the coils and/or the electrical terminals on the delivery catheter to make alignment more forgiving.

Additionally, visualization of the coil length during delivery can be challenging. Traditionally, radiopaque and biocompatible materials are necessary to use under fluoroscopy during endovascular treatment of aneurysms and other vascular diseases. Materials such as platinum, palladium and tantalum ore often used to provide a clear visualization of the implant during the procedure. However, when there are already multiple implants inside the aneurysm, the proximal end of the implant can become difficult to visualize among the mass of equally dense radiopaque implants.

It would thus be beneficial to provide an implant and a delivery system that have areas of varying radiopacity and/or radiotransparency such that various details of the implant and delivery system may be visualized under radio imaging such as fluoroscopy.

OBJECTS AND SUMMARY OF THE INVENTION

The present invention is directed to a variable detachment coil having multiple detachment junctions so that a user can detach a customizable length of the coil to occlude a treatment site.

One aspect of the variable length detachment coil is an improved electrical contact configuration associated with the coil.

In one embodiment the, contacts comprise electrical bumps on the coils that make electrical contact with the terminals of the delivery catheter.

In another embodiment, the contact comprises whisker-like electrical leads that radiate from the coils.

Another aspect of the invention is a visualization system incorporated into the coils that comprise radiotransparent ceramic discs that appear as spaces in the coil segments under X-ray. These discs allow visualization of the individual coil segments.

Another aspect of the invention is directed to a coil having multiple detachment points, each of which have a radiopaque and/or radiotransparent quality that allows a physician to visualize the various detachment points, so a selection is more easily made.

In one embodiment the variable length detachable coils have electrical contacts that are filaments extending from the coil segments.

In another embodiment the variable length detachable coils have electrical contacts that are beads protruding outwardly from the coil segments.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

It is noted that with respect to the Figures, elements on the left side of the drawings are considered distal relative to the elements on the right side of the drawings (and, consequently, elements on the right side of the drawings are considered proximal relative to the elements on the left side of the drawings).

Generally, the present invention relates to an embolic coil, also referred to as a variable detachment coil, and a detachment system employed on a delivery catheter. The variable detachable coil is made up of a coil separated into segments by detachment zones that are located in specific locations. The variable detachment coil system of the invention is distinguished from previous systems by advancements made in electrical connection features and its visualization features.

Electrical Connections

Figure 1:
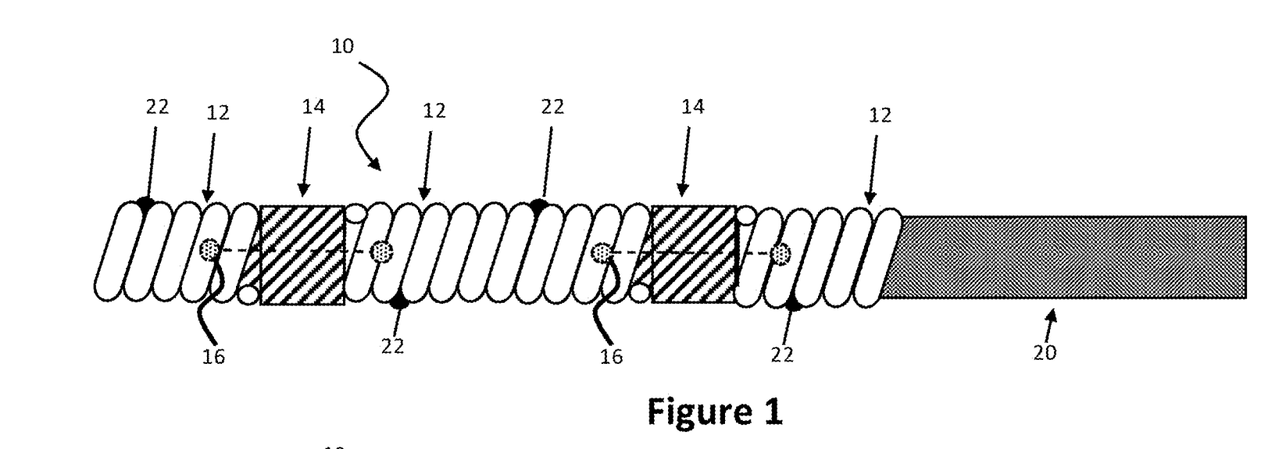
FIG. 1 is an elevation of an embodiment of an embolic coil and pusher used with a detachment system of the invention.

FIG. 1 is an illustration of an embodiment of a variable detachment coil 10 of the invention. The coil 10 includes a plurality of coil segments 12 separated by detachment capsules 14 between the segments 12. The length of segments 12 can be sized in various ways depending on the size of the occlusive treatment site and the number of coil segments 12 used along the variable detachment coil 10. In some illustrative examples, segments 12 are in the range of 1-10 cm, 2-4 cm, or 2-3 cm.

The detachment capsules 14 comprise links 16. The links 16 are degradable and, when the links are degraded sufficiently, the coil segment 12 detaches from the rest of the coil 10. Only three coil segments 12, separated by two detachment capsules 14, are shown in FIG. 1, but it is to be understood that this is for illustration purposes only and one practicing the invention could employ numerous (n) segments connected by a corresponding (n−1) number of capsules.

Links 16 may be either thermally degradable or electrolytically degradable. Thermally degradable links are degraded by heat whereas electrolytically degradable links degrade when electricity passes through them. The electrolytically degradable links thus do not require a heater.

The detachment capsules associated with the thermally degradable links thus include heater elements and have a degradable or detachable linkage (e.g., polymer monofilament) attached to either side on the inner diameter (ID) of the coils. The heater elements are electrically activated to generate heat to degrade/detach the linkage. The detachment capsules, as well as variable detachment coil concepts including capsules spaced periodically along the length of an embolic coil, are discussed in U.S. Pat. No. 9,877,729 entitled CATHETER SYSTEM, issued on Jan. 30, 2018 to Bowman et al., and in U.S. Pat. No. 9,808,599, entitled DEVICE DELIVERY SYSTEM, issued Nov. 7, 2017 to Bowman et al., both of which are hereby incorporated by reference in their entireties.

Figure 3:
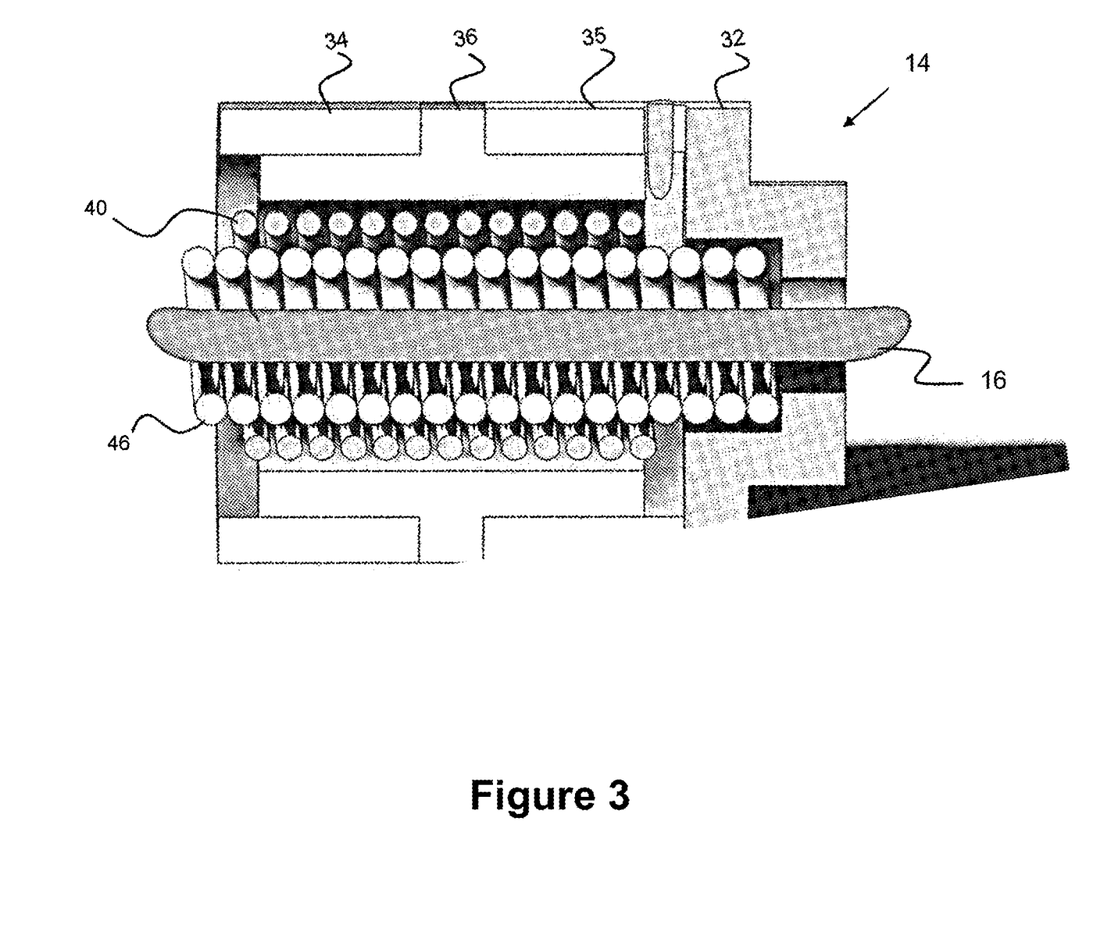
FIG. 3 is cutaway elevation of an embodiment of a detachment capsule of the invention.

Each detachment capsule 14, whether thermal or electrolytic, is thus activated using electricity. FIG. 3 shows a representation of a thermal detachment capsule 14a, according to one embodiment—though it should be noted various thermal and/or electrolytic capsules can be used which are discussed in more detail in the incorporated patents referenced above. The detachment capsule 14a includes a spring 46 that spans the entire capsule 14a and is located within a heater coil 40. A degradable monofilament 16 spans within and through the spring 46 and may be tied to a proximal part of the spring 46. A distal (right side) cap 32 connects to an adjacent coil segment 12 (not shown). The degradable filament 16 is tied at each end to the adjoining coil segment that sits on either side of the detachment capsule 14a. As electricity passes through the capsule 14a the heater coil 40 is energized and heats up, degrading the link 16 passing through the heater coil.

Please note the thermal detachment capsule 14a, shown and described with regard to FIG. 3 is meant to embody how a particular detachment capsule 14 could be designed. The incorporated references discuss more detachment and capsule-related embodiments, and the capsules can incorporate thermal or electrolytic concepts. Where thermal means are used, a degradable link (e.g., filament) would be used. Where electrolytic means are used, a degradable/corrodible wire (e.g., a fuse-link) would be used. In some embodiments, the capsule 14 can simply represent a general junction, such as a meltable adhesive, tether, or other severable member that is placed between two coil segments 12.

In order to provide electricity to the detachment capsule 14, each coil segment 12 includes two electrical contacts formed on an outer surface of the segment 12. In FIG. 1 the electrical contacts are embodied as conductive bumps or beads 22, which contact the electrical catheter terminal to create electrical communication between the capsule and the catheter terminal. One contact is placed at each end of the contact structure of the delivery system so that a circuit is created between the two ends of the capsule, this circuit is used to activate a degrading member such as a tether, meltable adhesive, electrolytically degradable linkage, or a variety of structures to degrade the degrading member in the capsule and detach the capsule, thereby detaching the embolic coil.

Looking again at FIG. 1, it is seen that an electrical contact in the form of a bead 22 is present on either side of each detachment capsule 14 and are used to convey electricity from the catheter terminals, described below, to the detachment capsules 14 via the coil segments 12. Thus, the coil segments 12 are used as conductors in the circuitry of the detachment system. The purpose of the bead 22 is thus to be slightly elevated from the coil 10 such that solid contact is made with the terminals of the detachment system. Care is taken to ensure that the beads 22 are not so large as to create excessive friction within the catheter 52 when the coil 10 is being pushed therethrough by a pusher 20.

Because the coil 10/coil segments 12 are being used as a conductor, the bead 22 can be placed anywhere along the coil, so long as it aligns with the terminal of the catheter. It is beneficial that the spacing between adjacent beads matches the spacing of the terminals to maximize the ease with which alignment may be made. Please note, this matching of space is less important in particular circumstances, for instance where the beads are smaller than the catheter terminal, thus allowing more room for the beads to make contact with the catheter terminals.

Figure 2:
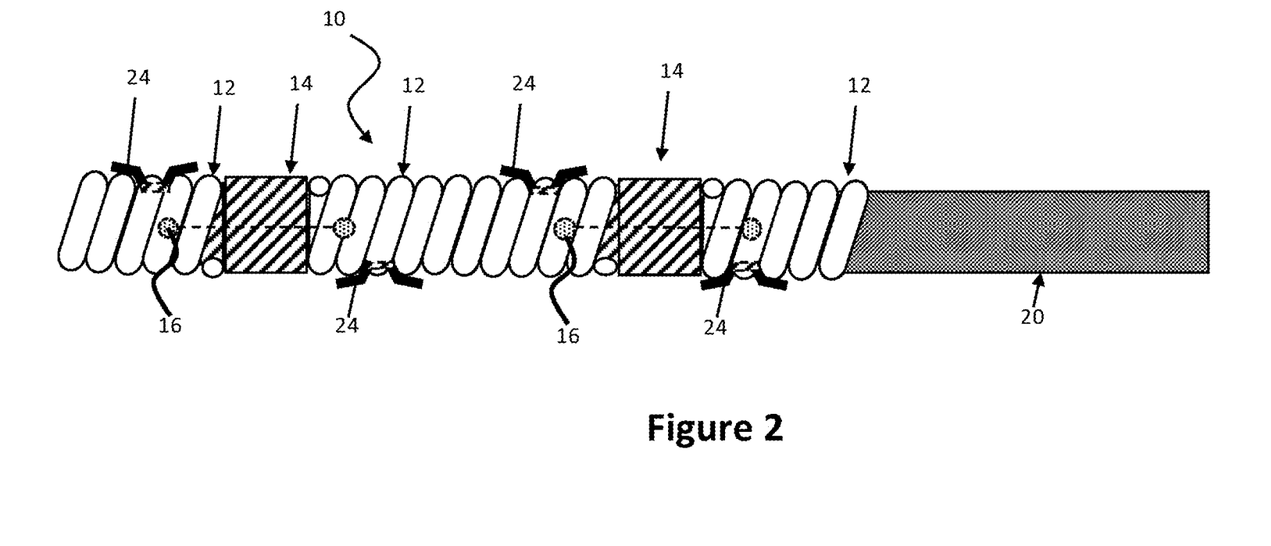
FIG. 2 is an elevation of an embodiment of an embolic coil and a pusher used with a detachment system of the invention.

FIG. 2 shows an alternative embodiment of the electrical contacts. The electrical contacts of FIG. 2 are provided in the form of conductive filaments 24 or wire segments that are woven through the individual loops of the coil segments 12 and protrude therefrom thus forming whisker-like electrical contacts. The filaments 24 may be flexible and slightly biased toward a radiating state such that as the coil 12 is pushed through the catheter 52, the filaments 24 bend and present little resistance to movement through the catheter. However, the filaments 24 maintain contact with the inner surface of the catheter such that when they enter the detachment system, positive contact is made with the terminals.

Like the beads 22 of the embodiment of FIG. 1, the filaments 24 are used to convey electricity from the catheter terminals, described below, to the detachment capsules 14 via the coils 12. Thus, the coils 12 are again used as conductors in the circuitry of the detachment system.

One advantage to using the beads 22/filaments 24 as a conductive contact and, in turn, using the coil as the conductor to the associated detachment capsules 14 is that the contact points can be spread out. In one example, a plurality of beads 22/filaments 24 can be used on each coil segment 12 and, in this way, there are a number of contact points between the overlying catheter contact terminals (discussed in more detail below) and the coil 10. In another example, the bead 22/filament 24 is considerably undersized compared to the overlying catheter contact terminals so that a larger section of the coil segment 12 is available to be in electrical communication with the catheter contact terminals. One advantage to this approach is that a user would not necessarily need a cue (e.g. a signal, such as a light) when the appropriate detachment junction is reached since a large part of the coil is available to act as a conductor. The user could simply confirm when a proper amount of coil has been delivered, then activate detachment of the coil.

Alternatively, the beads 22 or filaments 24 could be placed on the detachment capsules 14. The outer casing of the capsule 14 would then be electrically connected to one side of the heater coil 40 while the other side of the heater coil would be electrically connected to the adjacent coil segment 12, which would be connected on an opposite end to another detachment capsule 14 with a bead 22 or filament 24. Referring to FIG. 3, the capsule 14 is shown as having first and second conductive sleeves 34 and 35 with an insulating sleeve 36 disposed between them.

A proximal pusher 20 (e.g., an elongated member attached to the coil 10 so as to push the coil 10 out of a catheter) is connected to a proximal end of the coil 10 and may optionally include another link 14 between the proximal-most coil segment and the pusher, as shown in FIG. 2. The pusher 20 may be comprised of a hypotube or wire of similar dimensions to the coil 10 to allow easy tracking within the delivery device (e.g., microcatheter). The pusher 20 can be made of a metal such as stainless steel or Nitinol, or a polymer such as polyethylene or polyimide.

Figure 4:
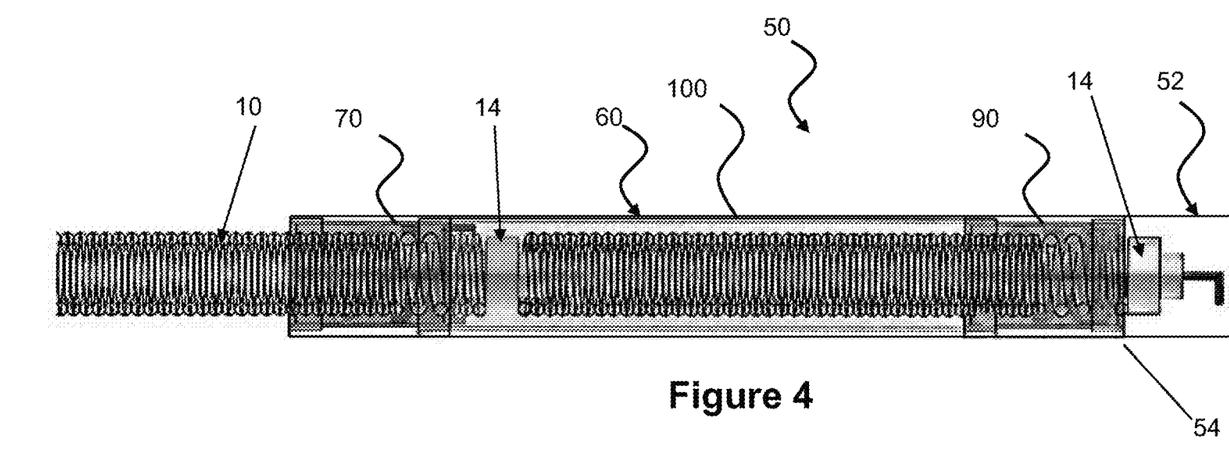
FIG. 4 is a transparent elevation of an embodiment of an embolic coil and a detachment system of the invention.
Figure 5:
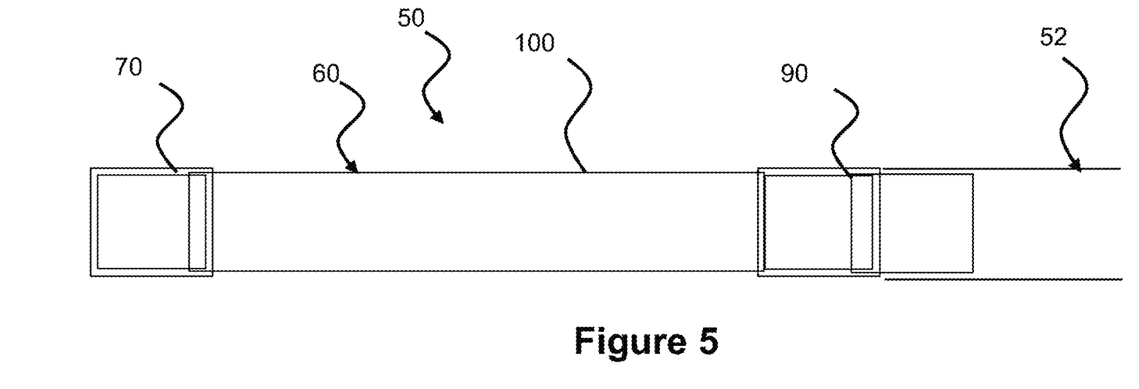
FIG. 5 is a transparent elevation of an embodiment of a detachment system of the invention.

The delivery system 50 of the invention is shown in FIGS. 4 and 5. The detachment system 50 comprises a catheter 52 and a detachment system 60 attached to a distal end 54 of the catheter 50. The detachment system 60 may be a separate structure connected to a distal end of the catheter, may be formed in the distal end of the catheter and integral therewith, or may be an insert that is contained within the distal end of the catheter. Ideally, however, an inner diameter of the detachment system matches the inner diameter of the catheter, with the possible exception of the electrical contacts of the detachment system. In this way the detachment system does not present a hinderance to the delivery of the coil.

The detachment system includes two electrical terminals, a distal terminal 70 and a proximal terminal 90. The two terminals 70, 90 are separated by an insulating connector or liner 100, which could also be a section of the catheter itself. The electrical terminals 70 and 90 are oppositely polarized. This polarization can be done in a number of ways; in one example a DC battery with a positive and negative terminal is used and wires span between the battery and the catheter contacts to polarize the contact, such that one catheter contact is positive, and one is negative. These wires, not shown in the figures, may be located within interior channels in the catheter, may be integrated into the catheter when the catheter is formed, or may reside in outer channels or on an exterior of the catheter. In one example the distal terminal 70 is positive and the proximal terminal 90 is negative. In another example the distal terminal 70 is negative and the proximal terminal 90 is positive.

The distal and proximal electrical terminals 70 and 90 may be tubular and may be constructed to have inner diameters that are slightly smaller than an inner diameter of the catheter 52 in order to better facilitate electrical connection with the contacts of the fuse wires. Alternatively, the inner diameters of the terminals may match the catheter 52 and reliance may rest with the electrical contacts 22 or 24 to make contact with the terminals 70 and 90.

Figure 6:
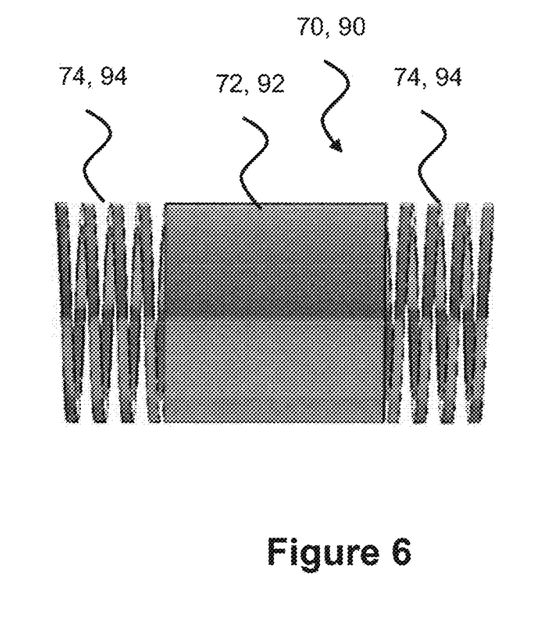
FIG. 6 is an elevation of a terminal of the invention.

One embodiment of a terminal 70, 90 is shown in FIG. 6. Terminal 70, 90 has a body 72, 92, and ends 74, 94. The ends are cut into spiral or helical coils, giving the ends a flexible, resilient quality that can be used to attach the terminal to adjacent structures such as the liner 100 or the catheter 52.

Figure 7:
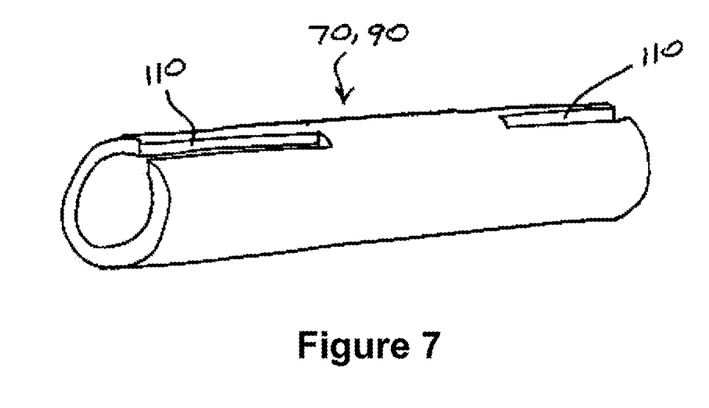
FIG. 7 is a perspective view of an embodiment of a terminal of the invention.
Figure 8:
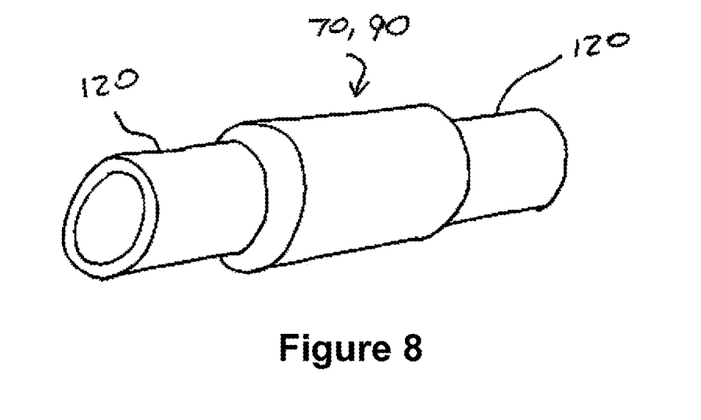
FIG. 8 is a perspective view of an embodiment of a terminal of the invention.

Alternatively, the terminal can be attached to the liner and/or the catheter inner lumen using a tube-like terminal structure having a small slot 110 at either end, such as the terminal 70, 90 shown in FIG. 7, or a step configuration 120 such as is shown on the terminal 70, 90 shown in FIG. 8. A combination of any two of these configurations may also be used.

Visualization Features

The aforementioned radiopacity/radiotransparency of the various components provides a clear picture to a physician as to the locations of the various segments as well as the locations of the proximal and distal terminals of the delivery device. Visual separation between the coils segments is accomplished through the use of radiotransparent spacers, as will be discussed in the upcoming inventive embodiments. The use of such radiotransparent spacers allows the operator to determine where the detachment junctions of the variable detachment coil are located, helping to visually locate these detachment elements.

Figure 9:
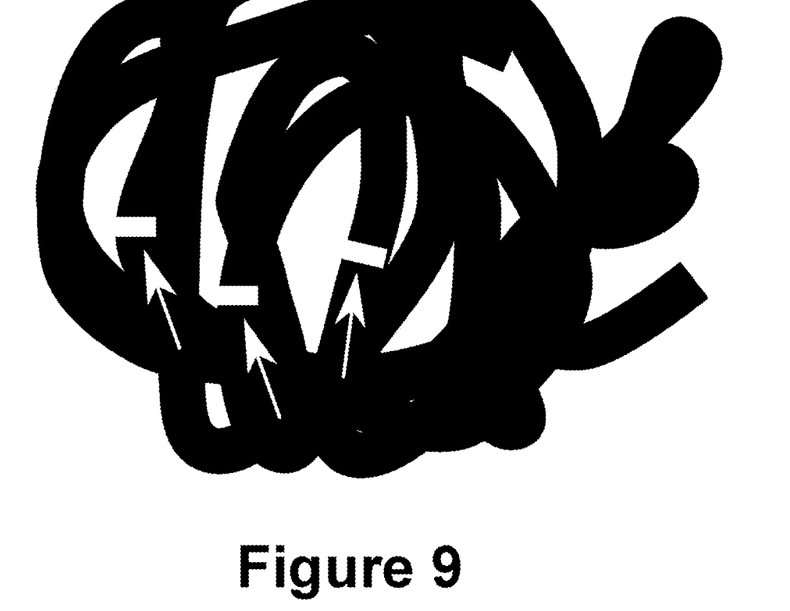
FIG. 9 is an image taken using X-ray of an embodiment of an implant of the invention.
Figure 10A:
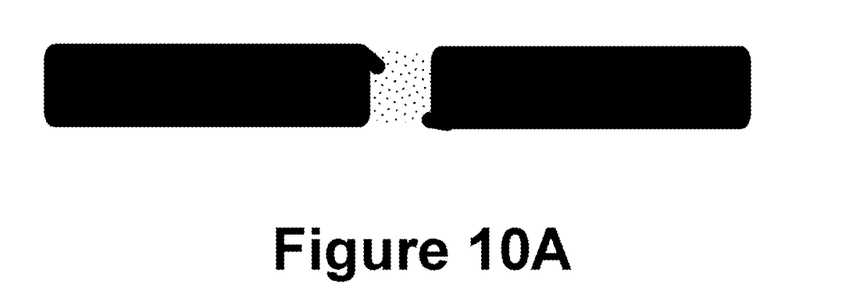
FIG. 10a is an image taken using X-ray of an embodiment of an implant of the invention.

Referring now to FIG. 9, there is shown an image of several implanted coils of the invention taken under X-ray. It can be seen that there are four coil segments separated by three radiolucent or radiotransparent links or capsules, indicated by the arrows. One embodiment provides a ceramic spacer 17 placed between adjacent coil segments. FIG. 10A is an X-ray image of a 0.010-inch-long ceramic disc placed between 2 platinum coils. Though ceramic is discussed as one radiolucent/radiotransparent option, any such radiolucent/radiotransparent material can be used. A non-exhaustive list includes ceramic, stainless steel or other non-radiopaque metals, and polymer (e.g., PET or PTFE).

Figure 10B:
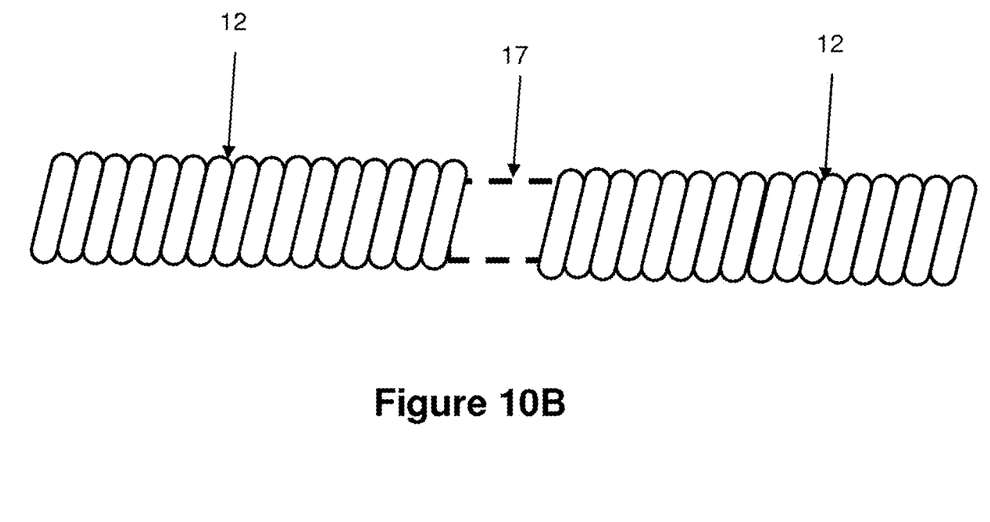
FIG. 10b is a line drawing of the image of FIG. 10a provided for clarity.

FIG. 10b is a drawing of the image of FIG. 9a to show detail. There is shown a coil segment 12 on either side of a radiolucent spacer 17.

Figure 11:
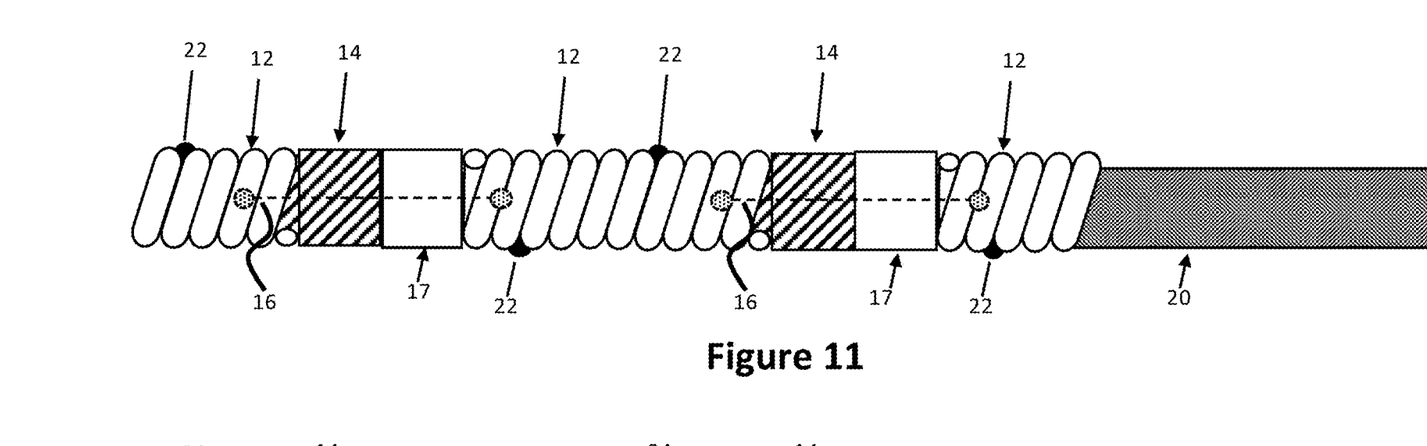
FIG. 11 is an elevation of an embodiment of an embolic coil and pusher used with a detachment system of the invention.
Figure 12:
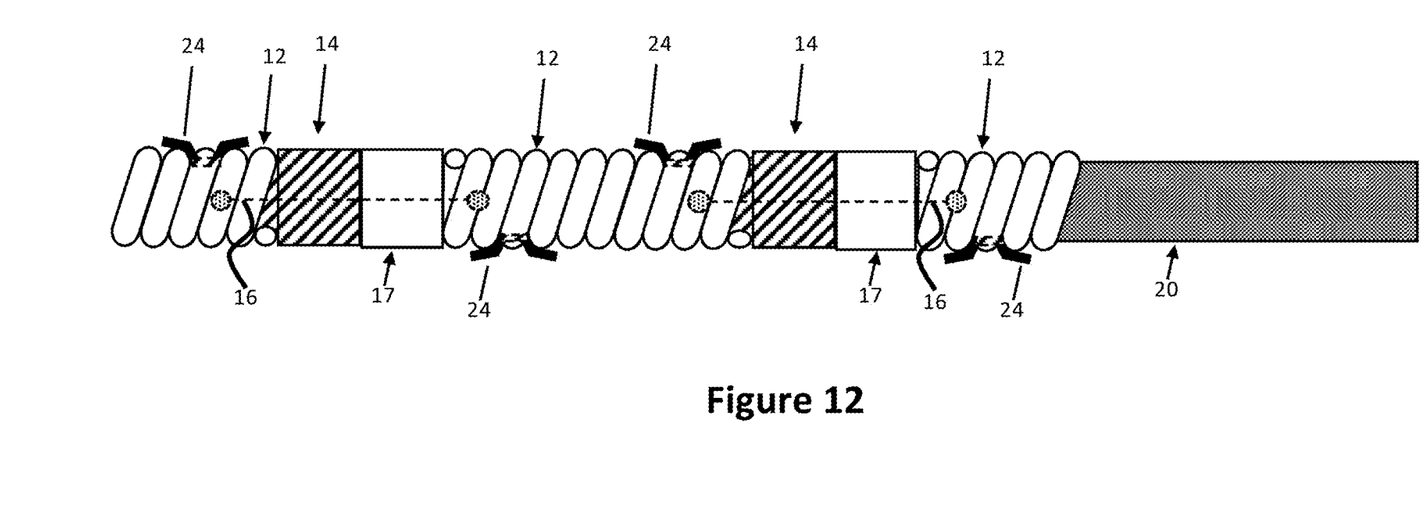
FIG. 12 is an elevation of an embodiment of an embolic coil and pusher used with a detachment system of the invention.

FIGS. 11 and 12 provide examples of how the spacers 17 may be incorporated into the detachment system of the invention. FIG. 11 shows the detachment system of FIG. 1, that incorporates detachment capsules 14 and contact beads 22 extending from the coils 12. The spacers 17 are illustratively deployed on the proximal sides of the detachment capsules 14, though the spacers 17 can be attached on either side of the capsules 14. These spacers 17 thus aid in aligning the detachment capsules 14 with the terminals 70 and 90 of the detachment catheter 50.

Similarly, FIG. 12 shows the detachment system of FIG. 2, that incorporates detachment capsules 14 and contact filaments 24 extending from the coils 12. The spacers 17 are also illustratively deployed on the proximal sides of the detachment capsules 14 (though the spacers 17 can be deployed on either side of the capsules 14). These spacers 17 similarly aid in aligning the detachment capsules 14 with the terminals 70 and 90 of the detachment catheter 50.

Figure 13A:
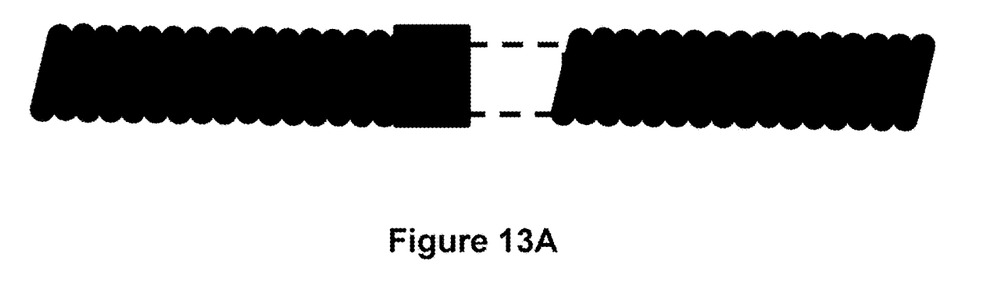
FIG. 13a is an image taken using X-ray of an embodiment of an implant of the invention.
Figure 13B:
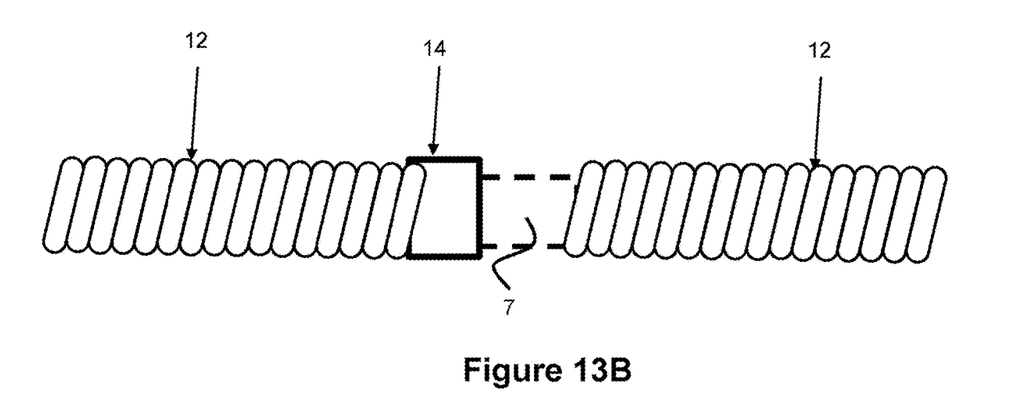
FIG. 13b is a line drawing of the image of FIG. 13a provided for clarity.

FIG. 13A is an image representing how the embodiment of FIGS. 11 and 12 would appear under X-ray. FIG. 13B is a line drawing of the image of FIG. 13A provided for clarity.

Figure 14:
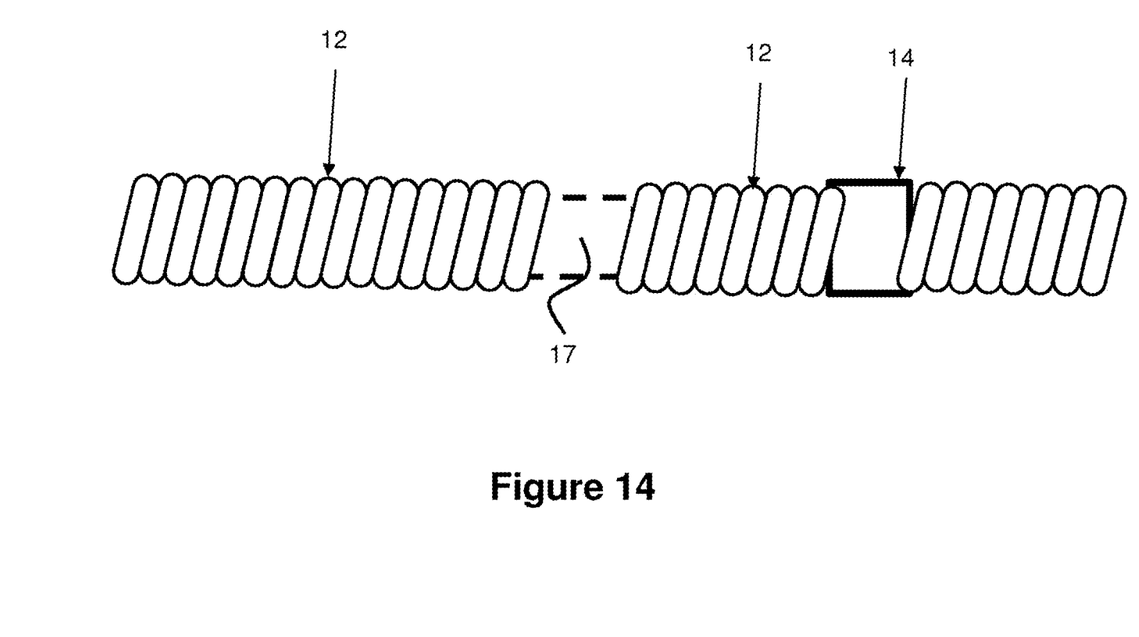
FIG. 14 is an elevation of an alternative embodiment of the device of FIG. 13b.

FIG. 14 shows an alternative arrangement in which the spacer 17 is longitudinally separated from the detachment capsule 14. This may be advantageous in cases where the detachment capsules 14 are hidden by the radiopaque terminals 70, 90. The placement of the marker band 17 would be alignable with a landmark on the delivery device, such as the distal end of the catheter 50 to signify that the detachment capsule is aligned under the terminal 70, 90.

Other less radiopaque metallic materials may also be useful in visualization. A cylindrical platinum or palladium marker band may blend in with the implant coil and look as one under fluoroscopy. However, if the marker band has gaps or cut-outs, the radiopacity of the component would be decreased, allowing for easier distinction between the coil segments.

Please note, the radiolucent spacers, discussed above, have particular utility in visualizing the detachment junctions. This could be useful in situations where, for instance, there is no cue (e.g., a light) when the detachment junction is reached—instead, the operator would just visually check where the detachment junction is presented and initiate detachment. These spacers are also helpful in situations where there is a user cue (e.g., a light) but it is not operational. Furthermore, coil deployment can be complicated since the coil adopts a wadded-type configuration once it is released into the treatment site, making it difficult to check the length of coil that is deployed. Adding these spacers can help gauge how much coil is deployed by providing a visual benchmark of approximately how many segments there, since each segment is separated by a spacer and these spacers will be visible.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A variable length detachable coil, comprising:
   a plurality of coil segments each having at least one electrical contact; and,
   a detachment capsule connecting an adjacent pair of the coil segments and electrically connected to the electrical contacts on the adjacent pair of the coil segments;
   wherein the electrical contacts are each fixed to and protrude from an outer surface of one of the plurality of coil segments.

2. The variable length detachable coil of claim 1, wherein the electrical contacts from the adjacent pair of the coil segments are spaced to align with electrical terminals within a lumen of a delivery device.

3. The variable length detachable coil of claim 2, where in a pre-detachment configuration, the electrical contacts of the adjacent pair of the coil segments, the detachment capsule, and the electrical terminals within a lumen of a delivery device form an electric circuit.

4. The variable length detachable coil of claim 3, where an electric current through the electric circuit disconnects the adjacent pair of the coil segments from each other to form a detached configuration.

5. The variable length detachable coil of claim 1, further comprising a plurality of detachment capsules, each being interspaced between one coil segment of a plurality of adjacent pairs of coil segments, and where in a selective pre-detachment configuration, the electrical contacts of a selected adjacent pair of the plurality of adjacent pairs of coil segments, a selected detachment capsule, and electrical terminals within a lumen of a delivery device form a selected electric circuit.

6. The variable length detachable coil of claim 5, where an electric current through the selected electric circuit disconnects the selected adjacent pair of coil segments from each other to form a selected detached configuration.

7. The variable length detachable coil of claim 1, wherein the electrical contacts comprise filaments extending from the coil segments.

8. The variable length detachable coil of claim 1, wherein the electrical contacts comprise beads connected to the coil segments.

9. The variable length detachable coil of claim 1, wherein the coil segments are between 2 and 4 centimeters in length.

10. The variable length detachable coil of claim 1, further comprising a non-radiopaque spacer positioned between the adjacent pair of coil segments.

11. A variable length detachable coil, comprising:
    a plurality of coil segments,
    wherein each of the coil segments is radiopaque;
    wherein at least one of the plurality of coil segments is connected by a detachment capsule that detachably connects a pair of the coil segments;
    wherein the at least one of the plurality of coil segments is non-detachably connected by a non-radiopaque spacer that is longitudinally separate from the detachment capsule; and,
    wherein the non-radiopaque spacer is comprised of a ceramic disc.

12. The variable length detachable coil of claim 11, wherein the non-radiopaque spacer is comprised of a radiotransparent spacer.

13. The variable length detachable coil of claim 11, wherein the non-radiopaque spacer is comprised of a radiolucent spacer.

14. The variable length detachable coil of claim 11, wherein the non-radiopaque spacer is positioned on a proximal side of the detachment capsule.

15. The variable length detachable coil of claim 11, wherein the non-radiopaque spacer is positioned between the detachment capsule and one of the pair of coil segments.

16. The variable length detachable coil of claim 11, wherein the detachment capsule forms an electrical circuit between electrical contacts on the pair of the coil segments, and wherein the electrical contacts are each fixed to and protrude from an outer surface of one of the coil segments.

17. A variable length detachable coil, comprising:
- a plurality of coil means for occluding a target structure, each having at least one electrical contact; and,
- a detachment means for selectively disconnecting the coil means, wherein the detachment means is connected between an adjacent pair of the coil means; electrically connected to the electrical contacts on the adjacent pair of coil means;
- wherein the electrical contacts are each fixed to and protrude from an outer surface of one of the plurality of coil means.

* * * * *